United States Patent [19]

Bowersock et al.

[11] Patent Number: 5,674,495
[45] Date of Patent: Oct. 7, 1997

[54] ALGINATE-BASED VACCINE COMPOSITIONS

[75] Inventors: Terry L. Bowersock; Kinam Park; Robert E. Porter, Jr., all of West Lafayette, Ind.

[73] Assignee: Purdue Research Foundation, West Lafayette, Ind.

[21] Appl. No.: 394,802

[22] Filed: Feb. 27, 1995

[51] Int. Cl.$^6$ .................... A61K 39/00; A61K 45/00; A61K 39/02; A61F 13/00
[52] U.S. Cl. .................... 424/184.1; 424/278.1; 424/234.1; 424/280.1; 424/281.1; 424/424; 424/434; 424/438; 424/480; 424/492
[58] Field of Search .................... 424/184.1, 278.1, 424/234.1, 280.1, 281.1, 282.1, 434, 424, 438, 480, 492, 813, 823; 530/817

[56] References Cited

U.S. PATENT DOCUMENTS

| | | | |
|---|---|---|---|
| 4,220,152 | 9/1980 | Dresback | 128/260 |
| 4,391,909 | 7/1983 | Lim | 435/178 |
| 4,798,786 | 1/1989 | Tice et al. | 435/177 |
| 5,352,448 | 10/1994 | Bowersock et al. | 424/438 |

FOREIGN PATENT DOCUMENTS

| | | |
|---|---|---|
| 127989 | 5/1984 | European Pat. Off. . |
| 188309 | 1/1986 | European Pat. Off. . |
| PCT/US91/ 00475 | 8/1991 | WIPO . |
| 9402170 | 1/1995 | WIPO . |
| 9502416 | 1/1995 | WIPO . |

OTHER PUBLICATIONS

Cohen et al. 1991. Proce. Natl. Acad. Sci. USA vol. 88: 10440–10444.

Offit et al. 1994. Virology, 203:134–143. "Enhancement of Rotavirus Immunogenicity by Micro.".

An influence of the structure of alginate on the chemotactic activity of macrophages and the antitumor activity. Michio Fujihara et al. *Carbohydrate Research*, 243, 211–216, 1993.

In vitro activation of human macrophages by alginate–polylysine microcapsules. Maria E. Pueyo et al. *J. Biomater. Sci. Polymer Edn*, vol. 5, No. 3, pp. 197–203, 1993.

Calcium Alginate Hydrogel as Matrix for Enteric Delivery of Nucleic Acids. Timothy J. Smith. *Pharmaceutical Technology*, pp. 26–30, Apr., 1994.

Long–term reversal of diabetes by injection of immunoprotected islets. Patrick Soon–Shiong et al. *Proc. Natl. Acad. Sci. USA*, vol. 90, pp. 5843–5847, Jun., 1993.

An Immunologic Basis for the Fibrotic Reaction to Implanted Microcapsules. P. Soon–Shiong et al. *Transplantation Proceedings*, vol. 23, No. 1, pp. 758–759, 1991.

Induction of Pulmonary Antibodies to Pasteurella haemolytica Following Intraduodenal Stimulation of the Gut–assocaited Lymphatic Tissue in Cattle. Terry L. Bowersock et al. *Can J Vet Res*, vol. 53, pp. 371–377, 1989.

Controlled Vaccine Release in the Gut–Associated Lymphoid Tissues. I. Orally Administered Biodegradable Microspheres Target the Peyer's Patches. John H. Eldridge et al. *Journal of Controlled Release*, vol. 11, pp. 205–214, 1990.

The Common Mucosal Immune System and Current Strategies for Induction of Immune Responses in External Secretions. Jiri Mestecky. *Journal of Clinical Immunology*, vol. 7, No. 4, 1987.

Recent Progress in Protein and Peptide Delivery by Noninvasive Routes. Lorraine L. Wearley. *Critical Reviews in Therapeutic Drug Carrier Systems*, vol. 8, pp. 331–394, 1991.

Liposomes Containing Anti–Idiotypic Antibodies: an Oral Vaccine To Induce Protective Secretory Immune Responses Specific for Pathogens of Mucosal Surfaces. Susan Jackson et al. *Infection and Immunity*, vol. 58, No. 6, pp. 1932–1936, 1990.

Stimulation of Immunity to Pasteurella Multocida in Rabbits by Oral Immunization using a Microsphere Delivery System. M.A. Suckow et al. *Proceed. Intern. Symp. Control. Ref. Bioact. Mater.* vol. 21, 1994.

Uptake of Alginate Microspheres by Peyer's Patches. T.L. Bowersock et al. *Proceed. Intern. Symp. Control. Rel. Bioact. Mater.* vol. 21, 1994.

Oral Administration of Mice with Ovalbumin Encapsulated in Alginate Microspheres. T.L. Bowersock et al. *Journal: Abstracts of Papers of the American Chemical Society*, vol. 208, Aug. 1994.

Diabetic Dogs Thrive with Islet Transplants. David N. Leff. *BioWorld Today*. vol. 4, No. 11, pp. 1 and 4, 1993.

Induction of Cytokine Production from Human Monocytes Stimulated with Alginate. Marit Otterlei et al. *Journal of Immunotherapy*, vol. 10, pp. 286–291, 1991.

Living Cure. Philip E. Ross. *Scientific American*, pp. 18–23, Jun. 1993.

Controlled release of water–soluble macromolecules from bioerodible hydrogels. J. Heller et al. *Biomaterials*, vol. 4, No. 4, pp. 262–266, Oct. 1983.

Biodegradable microparticles for oral immunization. O'Hagan et a. *Vaccine*;vol. 11, pp. 149–152, 1993.

Protective effects of an oral microencapsulated Mycoplasma hyopneumoniae vaccine against experimental infection in pigs. Weng et al. *Res Vet Sci*, vol. 53, pp. 42–46, 1992.

*Primary Examiner*—James C. Housel
*Assistant Examiner*—Jennifer Shaver
*Attorney, Agent, or Firm*—Barnes & Thornburg

[57] ABSTRACT

A vaccine composition including an antigen dispersed in an alginate gel is described. The alginate gel is preferably in the form of discrete particles coated with a polymer. Vaccination of vertebrate species can be accomplished by administering the alginate-based vaccine compositions orally.

17 Claims, No Drawings

ALGINATE-BASED VACCINE COMPOSITIONS

FIELD OF THE INVENTION

The present invention relates to a composition and method for vaccinating vertebrate species. More particularly, this invention is directed to a vaccine composition comprising a preselected antigen in an alginate gel and a method of vaccinating using said composition to induce immunity.

BACKGROUND AND SUMMARY OF THE INVENTION

Historically, immunization has relied on the induction of humoral immunity by parental administration of vaccines. Antibodies induced by parental administrations however do not necessarily reach mucosal surfaces, the sites of entry of most infectious agents. Mucosal immunity, which develops at mucosal surfaces as a result of contact of antigen with mucosal lymphoid tissues, is an important first line of defense against infectious agents. Secretory immunoglobin A (sIgA) is the predominant antibody isotype produced upon stimulation of the mucosa-associated immune system. sIgA prevents attachment of pathogens to the mucosal epithelium and neutralizes virus and bacterial toxins that can damage the host.

Induction of immunity at mucosal surfaces requires direct contact of antigens to a mucosal surface. However, this is not always possible or practical because of the handling/delivery problems or because the toxicity of the antigens to the mucosal surface. Mucosal immunity can be induced by the stimulating the mucosal associated lymphoid tissue (MALT), a network linking all mucosal sites to each other immunologically. Major concentrations of MALT are found in the upper respiratory tract (nasal associated lymphold tissue) the lower respiratory tract (bronchus associated lymphoid tissue) as well as the gut associated lymphoid tissue. When the mucosa-associated lymphoid tissue of the gut or lung is exposed to an antigen, lymphocytes migrate to all other mucosal sites and produce antibodies.

The greatest accumulation of lymphoid tissue in the common mucosal immune system and in the body is the gut-associated lymphoid tissue (GALT) located in the intestines. Peyer's patches are specialized areas of GALT containing functional T and B lymphocytes, macrophages and antigen-presenting accessory cells. The lymphoid tissue is separated from the lumen of the gut by a layer of epithelial cells which are interspersed with antigen-presenting accessory cells. These specialized accessory cells actively internalize samples from the lumenal space, and pass the samples to the underlying lymphoid cells. Exposure of GALT to antigen compounds triggers the clonal expansion of specific plasma (B lymphocyte) precursors and a population of memory lymphocytes which provide antibodies at a later time in response to the antigen. The antigen specific plasma precursors are influenced by $CD3^+$ $CD4^+$ and $CD8^-$ T helper cells located between follicles to preferentially produce sIgA.

In contrast to the systemic lymphoid tissues of the body, the B lymphocyte population of GALT includes a significant population of cells which are committed to the synthesis of IgA class antibodies. This antibody type is not effectively induced through conventional intramuscular or subcutaneous immunization. The IgA committed B lymphoblasts migrate through the mesenteric lymph nodes resulting in enhanced immune responses in all mucosal sites including the intestine, lung, mouth, eye, mammary gland, and the genitourinary tract. Thus, stimulation of GALT by oral vaccines can result in the prevention of infectious diseases at a variety of mucosal surfaces.

Orally administered vaccines are being studied intensively for delivery of vaccines for use in human diseases such as cholera, tetanus, influenza, and HIV using mice, guinea pigs, and baboons as experimental models. Development of vaccines for animals has a distinct advantage in that delivery systems and antigens can be tested for use in the target animal species for which the vaccines are intended. Hopefully, this will lead to quicker usage and acceptance of oral Vaccines. Information gained from oral vaccines developed for one species can be used for more efficient development of vaccines for other species. The development of RSV vaccines is an example where success in cattle could benefit humans and vice versa.

Oral administration of vaccines offers several advantages. Dosages could be administered to a large number of individuals via the food or water with minimal restraint and labor. Restraint also stresses animals rendering vaccination less effective thereby increasing the risk of infectious disease. Oral inoculation is quick and efficient. Formulations that could be used as one dose vaccines further eliminates the need for multiple handling of animals to administer subsequent booster inoculations. This is also an issue in human vaccination programs where compliance of patients to return to a medical center for second or third dose booster inoculations is poor. Adverse immune reactions following oral administration are also much less likely to occur and are therefore safer. For meat producing animals, oral administration has another advantage in that it avoids injection site reactions. Broken needles, contamination of the injection site, or the use of highly reactive adjuvants can induce abscesses that damage the carcass and the hides. These reactions decrease the value of the animal at slaughter.

Timely vaccination of livestock can be a critical aspect of effective farm management. Respiratory disease of viral and secondary bacterial etiology can spread rapidly through animal herds. Although stimulation of mucosal immunity can be achieved by intranasal administration or local injection into mucosal sites, such vaccination techniques typically require individual handling and restraint of each animal. Oral vaccination is a particularly cost effective way for livestock producers to vaccinate or treat a large number of animals at one time with minimal stress or labor. This is especially true when oral administration of the vaccine can be effected through ingestion by the animals during the course of feeding/drinking. Further, oral vaccines can be manufactured more cost effectively than parenterally administered vaccine formulations because of the fewer purification steps needed to generate an oral vaccine. Oral vaccination also offers the advantage of fewer side effects such as fever or other injection reactions.

Despite the advantages of oral vaccination, the development of oral vaccines has been delayed by the lack of adequate vaccine delivery systems. In the absence of suitable delivery systems, most oral vaccines, with the exception of cholera toxin (CT) and its nontoxic B subunit pentamer moiety, undergo degradation in the gastrointestinal (GI) tract resulting in limited absorption, which in turn results in insufficient immune responses.

Various delivery vehicles have been developed to deliver vaccine-relevant antigens to the gut-associated lymphoid tissues. Biodegradable polymers, such as poly(DL-lactide), poly(DL-lactide-co-glycolide) have been used to produce microparticles for oral administration of antigens. However, production of these polymer particles requires the use of solvents that can harm fragile antigens. Furthermore, the use of solvents prevents the incorporation of live organisms, such as viruses or bacteria, within poly(lactide-co-glycolide) microparticles.

The present invention makes use of alginate gels as a matrix for delivery of vaccine-relevant antigens. Alginates are a family of hydrophilic, colloidal polysaccharides extracted from seaweed and comprised of varying proportions of 1,4-linked β-D-mannuronic acid (M), α-L-guluronic acid (G), and alternating (MG) blocks. Alginate polysaccharides gel when combined/complexed with divalent cations. Alginates are known to have a wide variety of uses particularly as thickeners or emulsion stabilizers in manufacture of processed foods and pharmaceutical formulations. Alginates, as well as other polysaccharide gums, have been used to encapsulate living cells. Methods using alginates for encapsulating tissue and cells are described in U.S. Pat. Nos. 4,391,909 and 4,806,355, the disclosures of which are expressly incorporated herein by reference. Thus, for example, alginate matrices have been used to encapsulate beta islet cells. Upon injection into the peritoneum of mice, the encapsulated cells produced insulin and are protected from the body's attempt to reject the cells as foreign. The use of other polysaccharides, such as chitosan, for cell encapsulation is disclosed i U.S. Pat. No. 4,803,168, expressly incorporated herein by reference.

The present invention is directed to a vaccine composition which utilizes an alginate gel as a carrier and as an adjuvant for administering a vaccine relevant antigen. Thus, in one embodiment of the invention, there is provided a vaccine composition for oral administration to stimulate an immune response in a vertebrate species against a preselected antigen through contact with the antigen through a gut-associated lymphoid tissue of the vertebrate species. The composition comprises an effective amount of the antigen dispersed in an alginate gel. The alginate gel in the oral vaccine compositions of the present invention are preferably in the form of discrete particles, preferably microparticles, optionally coated with a polymer. The vaccine compositions are prepared utilizing basically the same methods described in the art for the use of alginate for encapsulating living cells. Essentially a solution of the antigen is substituted for the starting cell suspensions in the art-recognized cell encapsulation procedure. Further, polymer coatings are applied to the antigen-containing alginate gel particles using the same procedures described in the art for coating the alginate encapsulated cells typically utilizing ionic interaction of the negatively charged alginate surfaces with cationic (positively charged) polymers.

In another embodiment of the present invention there is provided unique vaccine compositions for oral administration to ruminant species. The ruminant vaccine composition also includes the coated, antigen-containing, alginate gel microparticles useful for vaccination of monogastric vertebrate species, but those particles are themselves dispersed in a solid hydrophilic carrier matrix which is formed to carry at least a portion of the dispersed particles into the post-ruminal portion of the digestive tract of ruminant species. The size and density of the hydrophilic matrix, which can include classical hydrogels or gelled alginate itself, is selected in accordance with the teachings in the art to promote rapid passage of the hydrophilic carrier matrix through the rumen into the post-ruminal portion of the digestive tract.

The present vaccine compositions are designed to present the antigen for contact with the gut-associated lymphoid tissue of the targeted vertebrate species to stimulate mucosal immunity. In another embodiment of this invention there is provided a method of stimulating a cell-mediated immune response in avian species by oral administration of the alginate-based vaccine composition.

The vaccine compositions in accordance with this invention are administered orally, typically with a pharmaceutically acceptable carrier, including, for example, water (e.g. animal drinking water), or utilizing gelatin capsules or other bolus dosage forms, or as a food additive to carry the alginate-based vaccine composition into the gut of the targeted vertebrate species.

DETAILED DESCRIPTION OF THE INVENTION

This invention relates to the use of alginate gels, most preferably in microparticulate form, for administration of vaccines. Vaccine-containing alginate microparticles have been shown to be effective for oral vaccination in several animal species. Use of the alginate-based vaccine delivery system in accordance with this invention have numerous advantages. First, the alginate gel vaccine delivery system eliminates the use of organic solvents or high temperature which are often required for the preparation of microparticles by other methods. By maintaining an aqueous environment and low temperatures throughout the preparation of the present alginate microparticles or microspheres, the present composition can include live bacteria and viruses, such as Bovine Respiratory. Syncitial Virus, *Pseudomonas aeruginosa* or *Pasteurella hemolytica*, as well as the more common antigens used for vaccines. Second, the alginate gel compositions are able to protect antigens/vaccines against degradation in the gastrointestinal tract. This allows stimulation of the same immune response with a smaller amount of antigen/vaccine. Further, the alginate system has itself been demonstrated to provide an adjuvant effect. Finally, alginate microparticles can be easily formulated for efficient delivery to both ruminant and non-ruminant species.

Oral delivery of vaccines using cross-linked poly (methacrylic acid) hydrogels has been shown to be effective in ruminants. See U.S. Pat. 5,352,448; expressly incorporated herein by reference. The hydrogels are made to have the appropriate size and density to pass quickly through the rumen thereby protecting the vaccine. The present alginate microparticles can thus be formulated for optimal use in ruminants, by dispersing them in hydrophilic carrier matrices such as classical hydrogels or preferably alginate gel matrices, for delivery of the microparticles to the post-ruminal portions of the ruminant digestive tract for contact with the gut-associated lymphold tissue.

The antigen-containing particles used in the vaccine compositions of the present invention are prepared using the same procedure and coating compositions described in the art for encapsulation of living cells. Such compositions are procedures are described, for example, in U.S. Pat. Nos. 4,391,909 and 4,806,355, the disclosures of which are expressly incorporated herein by reference. Alternate procedures and coating polymers are described in published European Application No. 0188309. In sum, a solution of the antigen and an alginate salt is sprayed into a solution of calcium chloride which effects gelation of the sprayed antigen/alginate droplets. Particle size can be controlled by controlling the size of the droplets of the alginate/antigen solution as they contact the calcium chloride solution. Alternatively, the alginate particles utilized in accordance with this invention can be made by adding calcium chloride to an alginate/antigen emulsion. Particle size can range from about 1 micron up to about 100 microns, more preferably between about 1 and about 30 microns, and most preferably between about 1 and about 15 microns. Excellent immune responses have been obtained by oral administration of alginate microparticles/microspheres, ranging in size from about 1 micron to more than about 30 microns. Given the reports in the art that microparticles between 1 and 10 microns are preferably absorbed by the Peyer's patches, the efficacy of the present orally administered alginate gel-based vaccine compositions cannot itself be explained by selective absorption on the Peyer's patches alone.

As in the case of the cell encapsulation technology described above, the antigen-containing alginate particles forming the basis of the present vaccine compositions are preferably coated with a polymer. The coating is typically applied simply by dispersing the alginate particles in a dilute solution of a polymer bearing functional groups that react with or show high affinity for the alginate surface. Any of a wide variety of polymers can be used, polylysine is particularly preferred because it is biodegradable and it shows high affinity for the surface of the antigen/alginate gel particles. Skilled practitioners in the art will recognize that other polymers, preferably cationic polymers, can be utilized using ionic interaction-based affinity to coat the alginate gel particles forming the basis of the present vaccine compositions. See again the relevant portions of U.S. Pat. Nos. 4,806,355 and 4,391,909.

The carrier matrix for the antigen/alginate particles in the ruminant vaccine composition of the present invention can be selected from any of a wide variety of hydrophilic polymers including, for example, synthetic polyacrylic acid based hydrogels and water soluble, natural or synthetic polysaccharide gums. Sodium alginate is the preferred water soluble gum. Other available gums include guar gum, gum arabic, carrageenan, pectin, tragacanth gum, xanthan gum, and acidic fractions thereof. Alginates provide a preferred hydrophilic carrier matrix for the ruminant vaccine formulations, particularly due to the ease of use of alginates for forming the ruminant vaccine compositions. Thus, a suspension of antigen/alginate microparticles, preferably coated with one or more polymers to provide either a positively charged or negatively charged surface, in a dilute (1–2% solution) of sodium alginate is introduced into an aqueous solution of calcium chloride. The size of the resulting carrier matrix pellets can be adjusted by the rate and method of delivery of microparticle suspension into the calcium chloride solution. Typically the resultant alginate pellets, each containing a dispersion of antigen/alginate microparticles, range in size from about 2 to about 8 millimeters, more typically about 4 to about 6 millimeters. The resultant macroparticulate (pellet-like) vaccine composition can be coated with one or more polymers using the same ionic interaction chemistry/polymers utilized to coat the microparticles as described above.

The vaccine compositions of this invention can be stored in aqueous suspension or in a dehydrated state for long periods of time without significant loss of antigenic activity.

The vaccine compositions in accordance with this invention can be administered orally as a component of drinking water, as a food additive, or as part of a vaccine formulation containing a pharmaceutically acceptable carrier and optional adjuvants. Pharmaceutically acceptable carriers for the alginate gel based vaccine compositions of this invention can include saline solutions or buffers or gelatin capsules. Alternatively, the present alginate gel based vaccine compositions can be included in other standard oral dosage forms, including those enterically coated to delay their dissolution in the gastrointestinal tract. Those skilled in the art will appreciate that there are wide varieties of art-recognized dosage forms and pharmaceutically acceptable carriers, suitable for delivering the antigen/alginate gel particles to the targeted portions of the digestive tract.

Administration of the vaccine compositions in accordance with this invention can be effected in single or multiple dose protocols. In one embodiment of this invention the vaccine compositions of this invention are administered in multiple dose protocols administered over a period of about 3 days to about 2 months or longer, and can be repeated periodically as the target species evidences loss of immunity.

Vaccine compositions produced in accordance with the present invention are administered either as a bolus or mixed with food or drinking water. For example animals can be vaccinated by including the vaccine compositions of the present invention a water bottle. In this application the water bottle is inverted so as the microspheres settle they are ingested by gravity as they entered the water nozzle. For applications for use in swine, poultry, and cattle, bubbles or oil can be incorporated in the vaccine composition of the present invention to increase the buoyancy (i.e., lower the density) of the vaccine compositions so that medicated watering devices used to administer other materials (antibiotics, wormers, etc) could be used to deliver the present vaccine/compositions. Administration of the antigen/alginate microparticulate compositions through the use of watering devices is a preferred route of administration for the following reasons: 1. Many farms are better equipped to administer materials through such medicators; 2. The FDA regulations are much easier to address (by producers of the vaccine); 3. Animals just entering a farm are already under stress are more likely to drink than to eat and since stressed animals are more at risk, the need to assure delivery of a vaccine is more critical; 4 For cattle, most water that is ingested bypasses the rumen so the loss of antigen in the rumen would be minimal. Thus, the antigen/alginate microparticulate composition of this invention can be administered to ruminants either as a component of the above-described ruminant vaccine compositions comprising a dispersion of the microparticles in a hydrophilic polymer carrier matrix or they can be administered as a component of ruminant drinking water.

Antigen delivery systems can be divided into two classes: live vectors and nonreplicating antigen carriers. The latter systems are easier to handle and are expected to have less complications than the former. Commonly used nonreplicating antigen carriers include microparticles, liposomes, oils, polymeric matrices, proteosomes, immune-stimulating complexes, conjugates of antigens with cholera toxin and its B subunit, and lectins. Each carrier has its own advantages and limitations. The present invention uses alginate microspheres to overcome problems associated with oral delivery of vaccines. Various delivery systems with different physical and physicochemical properties can be prepared depending on the specific needs of each vaccine, this technology provides a new means of effective delivery of vaccines by oral administration. Although alginate is used in the preferred embodiment, similar carbohydrate polymers could be used to achieve the same function of encapsulation of any antigen including live viruses or bacteria or parasites (protozoa or helminths, strongyles, etc.) in polymer particles. These include but are not limited to gelatin, dextran, hyaluronic acid, and starch. For production of microspheres of other polymers, the method of production would be altered. For example, for gelatin, the water soluble mixture containing the vaccine would be mixed and held at a temperature of 40° C. and mixed with oil at a similar temperature until the emulsion was produced. Once the emulsion is made, the temperature of the mixture would be reduced by packing the apparatus in ice. As the temperature falls, the gelatin microparticles would be solidified. They could then be stabilized by coating, for example, with poly-1-lysine.

EXAMPLE 1

Preparation of Alginate/Antigen Compositions

Sodium alginate, medium viscosity, (Kelco, Chicago, Ill.) is dissolved in water at a 2% w/v concentration with low heat and constant stirring. Once the powder is in solution it can be stored indefinitely as a liquid at 4° C. Antigen is dissolved (or suspended) in water or saline and added to the alginate to create a final mixture of alginate of 1.2% w/v. The alginate antigen mixture is placed in a syringe pump (Harvard Instruments, South Natick, Mass.), and infused into an atomizer (Turbotak Inc, Ontario, Canada). The alginate is sprayed into a 0.5% $CaCl_2$ solution placed 50 cm from the tip of the atomizer. Particles are separated from the $CaCl_2$ by low speed centrifugation, placed in a solution of poly-1-lysine (9600 mw to 150,000 mw, Sigma, St. Louis) with stirring for 20 minutes. The particles are sonicated to reduce clumping, washed 2 times in 100 times the volume of water to remove non-bound poly-1-lysine, and placed in $CaCl_2$ until used.

An alternative method of forming alginate/antigen microspheres utilizes an oil and water emulsion. An alginate/antigen mixture is prepared as describe above and combined with an oil, such as canola oil, and the combined elements are stirred at a high speed using a mixer. Once an emulsion is produced, $CaCl_2$ is added with stirring. The $CaCl_2$ binds to the droplets of alginate forming solid particles of a size less than 10 microns in diameter. The microparticles are then coated with poly-1-lysine.

Microspheres formed by either process can optionally be dispersed within larger alginate particles for administration to ruminant species.

Antigen release from microspheres—Microspheres containing a known amount of ovalbumin were placed in a microfuge tube containing phosphate buffered saline (pH 7.2). At 24 hour intervals, the buffer was removed and assayed for total protein content. A fresh aliquot of buffer was then placed on the microspheres. The eluents were tested for protein content using the biochinic acid (BCA) method (Pierce Chemical Company kit, Rockford, Ill.). Results showed that 44% of the protein was released at day 4. A total of 99% of the total expected load of protein was detected in the eluents by day 5. These results demonstrate that alginate microspheres will release the incorporated antigen load over time in vitro.

EXAMPLE 2

Viability of Alginate Encapsulated Bacteria

*Pseudomonas aeruginosa* was cultivated and diluted in saline to $10^{10}$ CFU. Bacteria was added to the alginate to create an alginate solution 1.0% w/v. For this study, a 23 gauge needle was used to drop the alginate into a calcium chloride 0.1 mM solution. Microspheres 1000–2000 μm in size were formed. To test viability of bacteria over time, microspheres containing bacteria were placed in a beaker of water in 1) a 37° C. incubator, 2) 4° C. cold room, air dried and placed 3) either at 37° C., or 4) 4° C., or 5) lyophilized and kept at 4° C. Approximately once a week an aliquot of microspheres was removed from each sample, placed in 0.1% w/v EDTA to break down the alginate, and the number of live bacteria quantitated by making serial dilutions of the dissolved alginate microspheres, and streaking 100 μl of each dilution on a blood agar plate. The agar plates were incubated overnight at 37° C. and the number of colonies counted. Results are shown below in Table 1.

TABLE 1

Number (in logs base 10) of *Pseudomonas aeruginosa* present in microspheres stored under different conditions over time.

| | Day | 7–8 | 17–18 | 21–24 | 31–36 | 42–45 |
|---|---|---|---|---|---|---|
| Gel conditions | | | | | | |
| air dry 37° C. | | 8 | 4 | | | |
| air dry 4° C. | | 4 | 7 | 7 | | |
| wet 37° C. | | | 7 | 5 | 3 | |
| dry 4° C. | | | | 6 | 7 | <3 |
| freeze dried –1% alginate | | 6 | 6 | 6 | | |
| freeze dried –.75% alginate | | 5 | 5 | 5 | | |

These results show that a live bacterium can survive in microspheres, especially if kept refrigerated, for an extended length of time (6–7 weeks).

Respiratory Syncitial Virus Incorporation in Alginate Microspheres—Respiratory syncitial virus (RSV) was grown in bovine turbinate cells in vitro. Virus was harvested and separated from cells and concentrated to $10^6$ TCID using tangential flow ultrafiltration (Minitan, Millipore Corporation, New Bedford, Mass.). Virus was suspended in tissue culture media, and mixed with 2% w/v alginate to make a final concentration of 1.2% w/v alginate. The microspheres were produced as described in Example 1 using a 0.5% $CaCl_2$ solution for polymerization. Microspheres were then washed in water and placed on bovine turbinate cells in tissue culture medium without serum. Cells were observed visually each day for signs of cytopathicity. By days post exposure, typical syncitial formation was observed in bovine turbinate cells. Viable virus was confirmed by staining infected cells with fluorescent antibody to RSV. These results show that not only can viable bacteria and tissue culture cells be incorporated within alginate, but RSV viruses as well.

EXAMPLE 3

Uptake of Alginate Microspheres by the Peyer's Patches

Animals—Six month old male New Zealand rabbits weighing 2.5–3.0 kg were used. Rabbits had pelleted feed and water ad lib.

Microparticle production—Microspheres were produced as described in Example 1. A 2.0 96 (w/v) solution of sodium alginate containing 1 mg/ml of bovine serum albumin labeled with fluorescein isothiocyanate (FITC) (Sigma, St. Louis, Mo. U.S.A.) was used by a syringe pump (Harvard Instruments, South Natick, Mass., U.S.A.) into an atomizer (Turbotak Inc, Waterloo, Ont., Canada) and sprayed into a 0.5% $CaCl_2$ solution. Microparticles were crosslinked with FITC-labeled poly-L-lysine (Sigma, St. Louis, Mo.,) to enhance their stability, to add a positive charge to their surface, and to enhance the fluorescent signal for detection of particles in the Peyer's patches.

Uptake of microparticles by Peyer's patches—Each rabbit was administered a mixture of ketamine and xylazine to induce a surgical plane of anesthesia. The abdomen was opened and individual Peyer's patches identified and isolated by ligating the intestine on each side with string. A solution of FITC-labeled alginate microspheres was injected into the ligated section of gut including the Peyer's patch until the lumen was distended. A total of 1 to $4 \times 10^7$ particles was injected into each ligated section of gut. The intestine was kept moist with phosphate buffered saline solution (PBSS). After 20 minutes each Peyer's patch was removed from the rabbit, the lumen of bowel opened and washed in PBSS to remove ingesta and unabsorbed microparticles. Each Peyer's patch was cut into 2 mm wide strips, placed into freezing compound (OCT, Miles Lab., Elkhart, Ind., U.S.A.), quick frozen in liquid nitrogen, and placed into a −70° C. freezer. Frozen sections 8 μm thick of each Peyer's patch were prepared and examined under a fluorescence microscope (Olympus BH-2, Lake Success, N.Y., U.S.A.).

Alginate microparticles were produced consistently of a size that could be absorbed by dome epithelial cells of Peyer's patches. Analysis of particle size indicated that the size of particles in general varied from 1 μm to over 30 μm in diameter, but with 70% of particles less than 10 μm. The shape of the particles varied but most were spherical. The microspheres were highly fluorescent and very stable with intense fluorescence for at least 1 month after preparation with minimal leakage detected.

Microspheres were seen in close apposition to the dome epithelium of the Peyer's patches of rabbits following inoculation into the lumen of the intestine. Some microspheres taken up by Peyer's patch were detected in the submucosa.

EXAMPLE 4

Oral Administration of Alginate Encapsulated Ovalbumin to Mice

Ovalbumin was orally administered to mice to test the efficacy of the present compositions to induce an immune response.

Animals: Ten–twelve week old female BALB/C mice obtained from the Purdue biological science facility were used. Mice were housed in the biological science building with food and water ad libitum. Each experimental group was housed in a separate cage.

Microparticle production: Ovalbumin was incorporated into alginate microspheres as follows: A 2.0% (w/v) Solution of sodium alginate containing 1 mg/ml of ovalbumin (Sigma, St. Louis, Mo., USEA) was infused by a syringe pump (Harvard Instruments, South Natick, Mass., U.S.A.) into an atomizer (Turbotak Inc., Waterloo, Ont., Canada) and sprayed into a 0.5% $CaCl_2$ solution. Microparticles were coated with poly-1-lysine (Sigma, St. Louis, Mo., U.S.A.) to enhance stability and to add a positive charge to their surface.

Inoculation of mice: Four groups of 3 mice each were inoculated as follows: 1) ovalbumin (OVA) in alginate microspheres, administered orally, 2) OVA in alginate microspheres, administered subcutaneously (SC), 3) antigen free alginate microspheres administered orally, and 4) OVA in complete Freund's adjuvant (CFA) administered SC. Mice were inoculated at 0 and 3 weeks with the antigen and route indicated. Each dose was administered a total volume of 100 ul. For oral administration mice were first given bicarbonate in saline to neutralize the stomach pH. Microspheres were then suspended in sterile water and administered by oral feeding needle directly into the stomach of each mouse. At week 4 each mouse was euthanized and serum and spleen cells harvested. A bronchoalveolar lavage (BAL) was also perform on each mouse at the time of euthanasia. For the BAL the lung and trachea were dissected out of the mouse and anterior end of the trachea clamped shut. A needle on a syringe was injected into the trachea and 1.0 ml of saline infused gently to expand the entire lung. The fluid was then gently withdrawn into the syringe, clarified by low speed centrifugation to remove cells, and the fluid frozen at −20° C. until assayed.

Immunological assays.—Serum and bronchoalveolar lavage fluids were assayed for IgG and IgA by ELISA. ELISA was performed using OVA absorbed to polystyrene plates. Samples were placed in wells in triplicate at a 1:25 dilution for serum and undiluted for BAL fluids. Goat anti-mouse antibody conjugated with horse radish peroxidase was used (Bethyl Laboratories, Montgomery, Tex., U.S.A.) followed by orthophenyldiamine substrate (Sigma, St. Louis, Mo., U.S.A.). Optical density of each well was determined by placing the plate in a microtiter plate spectrophotometer (Titertek, Multiscan, ICN/Flow Laboratories, Costa Mesa, Calif., U.S.A.) and reading the plate at 490 nm. Spleen cells were tested for antibody secreting cells (ASC) specific for OVA using techniques described previously.

Results

The OVA specific IgG and IgA antibodies were quantified by determining the increase in optical density over time (Table 2). There was an increase in OVA specific serum and IgA IgG for each mouse inoculated with OVA regardless of the route of administration. No OVA specific IgG or IgA antibodies were detected in the BAL fluids from any mouse. The number of OVA specific ASC per $10^6$ spleen cells is reported also in Table 2.

TABLE 2

Immune response of mice following oral or subcutaneous administration of ovalbumin in alginate microspheres

| Inoculation | Serum IgG (ΔO.D.) | Serum IgA (ΔO.D.) | ASC/$10^6$ Cells |
|---|---|---|---|
| OVA in MS - oral | 181 ± 52 | 113 ± 12 | 38 ± 10 |
| OVA in MS - SC | 424 ± 400 | 152 ± 47 | 52 ± 53 |
| OVA/CFA - SC | 131 ± 116 | 214 ± 112 | 272 ± 10 |
| OVA/alum - SC | 288 ± 313 | 129 ± 146 | 117 ± 42 |
| OVA in MS + CT - oral | 159 ± 123 | 85 ± 77 | 0 |
| Antigen-free MS - oral | 0 | 0 | 0 |

ΔO.D.: Change in optical density
ASC: Antibody secreting cells (all isotypes of antibodies)
OVA: Ovalbumin
MS: Microspheres
SC: Subcutaneous
CFA: Complete Freund's Adjuvant
Alum: Aluminum hydroxide adjuvant
CT: Cholera toxin Mice inoculated with ovalbumin in alginate microspheres by oral administration had a good immune response with increased serum IgG and IgA titers as well as antibody secreting cells in the spleen as shown in Table 2. The level of the immune response by oral administration was about the same as that by subcutaneous administration of ovalbumin in microspheres. Microspheres apparently released antigen in vivo to stimulate an immune response. The immune responses seen in mice inoculated with ovalbumin in complete Freund's adjuvant (CFA) or aluminum hydroxide adjuvant were similar to those obtained using the alginate microspheres. This suggests that alginate itself acts as an adjuvant. It is interesting to note in Table 2 that the incorporation of cholera toxin within the microspheres did not result in further increase in immune response over that obtained using alginate microspheres. This may be due to a few factors. First cholera toxin does not increase the response to all antigens, and ovalbumin may be one that does not respond. Second, there are differences in the response to cholera toxin by various strains of mice. And third, the adjuvant effect of the microspheres themselves may have made further enhancement harder to demonstrate. In any case, the mouse studies clearly show that the alginate microspheres are quite effective in inducing an immune response upon oral administration. These results suggest that there is little difference in the route of administration of antigen in the induction of serum IgA. The IgA detected in the serum after subcutaneous injection may be monomeric, while IgA after oral vaccination is usually polymeric.

EXAMPLE 5

Oral Administration of Alginate Encapsulated Antigens to Chickens

*Salmonella enteritidis* is a major cause of disease in laying hens. Infection decreases production and increases mortality in flocks. Moreover, *S. enteritidis* can be passed through the egg to baby chicks infecting subsequent generations, or humans who consume infected eggs. It is desirable to control this infection in birds to prevent both spread of disease in chickens and infection of consumers as well. Since infection begins by this bacteria attaching and invading the intestinal mucosa, and long term infection involves infection of intestinal lymphoid tissues, stimulation of mucosal immunity is imperative to control this disease.

To assess the efficacy of vaccinating chickens with the vaccine compositions of the present invention the flagellin of *S. enteritidis*, a key immunogen, was incorporated within alginate microspheres and administered orally to chicks. Ten-week old chickens received 3 oral doses at 2 week intervals of aliginated gel microspheres loaded with either 300 µg of flagellin antigen of *Salmonella enteritidis* or bovine serum albumin (BSA). One week after the last oral dose of antigen, serum and intestinal fluid were collected and assayed for flagellin specific antibodies by ELISA.

A cell mediated immune response, the delayed type hypersensitivity (DTH), was measured by challenging birds with an intradermal injection of 0.4 µg of flagellin in 0.1 ml of phosphate buffered saline in the right lateral toe web 2 weeks after the last oral dose of antigen. The left lateral toe web was inoculated with 0.10 ml of buffered saline. Toe web thickness was measured 48 hours later and the thickness of the saline injected web subtracted from the antigen injected web.

Results showed no significant difference in antibody titers to flagellin between groups of birds. However, the flagellin vaccinated birds had significantly increased DTH response. The flagellin vaccinated chickens had a mean toe web thickness of 38.0±6.3 and the control birds had a mean of 7.0±2.3 mm. This is unexpected for immunization using a soluble antigen such as flagellin. However, incorporation of the flagellin within the microspheres would change the presentation of the antigen making it more particulate and stimulating a MHC I response characterized by the increased DTH. This is an important immune response for this disease since *S. enteritidis* invades leukocytes and is retained for long term infection within these cells. Only cell mediated immunity such as DTH can help a bird clear this long term carrier state.

EXAMPLE 6

Oral Administration of Alginate Encapsulated Antigens to Calves

The efficacy of orally administered ovalbumin containing alginate microspheres prepared In accordance with the present invention to stimulate an immune response in the lungs of calves was investigated.

Ovalbumin was incorporated within alginate microspheres as described in Example 4. For oral administration to calves, the microspheres were encapsulated in a carrier matrix for bypassing the rumen and entry into the post ruminal portion of the gastrointestinal tract. Alginate microspheres prepared in accordance with the present invention were washed 2 times in distilled water, and suspended in water. This suspension of microspheres was added to a 2% solution of alginate with constant stirring at 20° C. A quantity of microspheres was mixed that contained the desired dose of ovalbumin. For a typical experiment, there was 40 µg of ovalbumin per µl of microspheres. Four calves were used per experiment and each calf received 5 mg of ovalbumin per dose for 5 consecutive days.

For each experiment a total of 2.5 ml of microspheres containing 20 doses, or 100 mg of ovalbumin total, were suspended in 15 ml of water. These were gently sonicated to break up clumps and then mixed with 100 ml of 2% alginate with constant stirring at 20° C. to create a suspension of microspheres within alginate. Aliquots of this suspension were dropped by 14 gauge needle and syringe into a vessel containing 0.5% $CaCl_2$. This technique produces alginate spheres 3–5 mm in diameter with a specific gravity of 1.1–1.4. The solid spheres (5 ml volume equal to a 5 mg dose) were then placed inside a ¼ ounce empty gelatin capsule. One capsule was administered to each calf per dose using a balling gun.

Four groups of calves were used to assess the efficacy of orally administered ovalbumin containing alginate microspheres to induce an immune response. Group 1 was given 2 doses of ovalbumin in an incomplete Freund's adjuvant by subcutaneous (SC) injection 3 weeks apart. This group was the parenteral control, the method of vaccination routinely used for any vaccine. Group 2 was given the same SC inoculations but also received 3 intrabronchial (IB) inoculations at day 14, 28, and 35. This technique was used to stimulate optimal local immunity in the lung. Direct inoculation stimulates the best immunity but is impractical for routine usage. Group 3 received 1 SC dose of ovalbumin followed by 2 oral regimens of ovalbumin. Each regimen consisted of one bolus containing 5 mg of ovalbumin in microspheres per day for five consecutive days. The second regimen was given 3 weeks after the first. Group 4 received 2 oral regimens of microspheres containing ovalbumin 3 weeks apart. Calves underwent bronchoalveolar lavage at day 0, at 1 week after the first oral regimen (about day 21), and 1 week after the second oral regimen (day 42). Another BAL was performed following an IB challenge of 5 mg of ovalbumin in orally vaccinated calves at day 54. Control (non-vaccinated) calves were challenged IB and lavaged 5 days later. BAL fluid and serum were evaluated for isotypic antibody response to ovalbumin. BAL cells were assayed by ELISPOT for antibody secreting cells (ASC) specific for ovalbumin. Table 3 shows the number of ovalbumin-specific antibody secreting cells (ASC) per million lymphocytes in bronchoalveolar lavages (BAL) obtained 42 days after the inoculation. The largest number (which is 486) of ASC for $IgG_1$ was observed with Group 3 which was inoculated with one subcutaneous (SC) dose of ovalbumin followed by 2 oral regimens of ovalbumin in microspheres. Calves in Group 2 (primed with SC followed by 3 intrabronchial inoculations) also showed a large number of $IgG_1$ ASC were detectable only in group 2 calves. Group 2 calves Sectert showed the largest number of IgA-ASC while only a small number of IgA-secreting cells were observed in Group 4 which were inoculated with 2 oral administrations. Although the oral inoculated group did not have a large number of IgA-secreting cells at day 42, there was a marked increase in IgA in the bronchoalveolar lavage fluids (see Table 4). This suggests that although a large number of IgA secreting cells were not detected, a significant amount of OVA specific IgA was produced in the lungs of these calves.

Table 4 shows the $IgG_1$ and IgA titers as detected by ELISA. Table 4 shows the data for $IgG_1$ is found primarily in blood as well as in alveoli, while IgA is mainly found in large airways like bronchi. In BAL fluids, $IgG_1$ increased in time in both Groups 3 and 4. On the other hand, the IgA response was not significant at day 20 but was the predominant antibody isotype present at day 42. About the same level of IgA was maintained at Day 54. Although the level of IgA at day 42 in Group 4 (which were inoculated by 2 oral administrations of OVA in microspheres) was not as high as that in Group 3 (inoculated by SC followed by oral vaccination), a very high level of IgA indicates that oral vaccination using alginate microspheres was quite effective.

TABLE 3

Number of ovalbumin specific antibody secreting cells per $10^6$ lymphocytes from bronchoalveolar lavages of calves inoculated with ovalbumin in microspheres

| Antibody Isotype | Inoculation Group | | | |
|---|---|---|---|---|
| | SC + SC | SC + IB | SC + Oral | Oral + Oral |
| $IgG_1$ | 2 | 148 | 486 | 23 |
| $IgG_2$ | 2 | 5 | 178 | 0 |
| IgM | 0 | 7 | 0 | 0 |
| IgA | 7 | 667 | 33 | 7 |

SC: Subcutaneous
IB: Intrabronchial
Oral: Within alginate microspheres

TABLE 4

Increase in absorbance values for BAL $IgG_1$ and IgA compared to Day 0

| | Antibody Isotype | | | | | |
|---|---|---|---|---|---|---|
| | $IgG_1$ | | | IgA | | |
| Group | Day 21 | Day 42 | Day 54 | Day 21 | Day 42 | Day 54 |
| Control | 35* (30)** | 75 (21) | | 0 | | 0 |
| SC + Oral | 201 (153) | 610 (57) | | 0 | 1059 (85) | 787 (174) |
| Oral + Oral | 103 (47) | 214 (27) | 273 (30) | 50 (10) | 349 (199) | 366 (319) |

*Mean
** Standard Deviation

These results show that ovalbumin encapsulated within microspheres and administered orally was able to stimulate an IB immune response in calves. SC priming dramatically increased the $IgG_1$ and IgA responses in orally vaccinated calves. No ASCs were detected for any isotype in the control calves. The increase in IgA in the BAL cells was significantly greater than in SC vaccinated calves. Response in calves as measured by ELISA to orally administered ovalbumin was similar to that seen in calves inoculated with SC plus IB inoculation. Calves inoculated with ovalbumin by oral administration within microspheres had greater $IgG_1$ and IgA responses in BAL fluids and in ASC assays than SC inoculated calves. These results show that ovalbumin administered within microspheres is able to stimulate a mucosal immune response in the lungs of cattle.

EXAMPLE 7

Oral Administration of Alginate Encapsulated Antigens to Rabbits

*Pasteurella multocida* is the most common bacterial pathogen of domestic rabbits. Although infection may be subclinical, disease characterized by rhinitis, pneumonia, metritis, septicemia, and otitis media may occur. Significant losses from disease are incurred by breeders and users of rabbits for research or show.

It has been previously described that intranasal immunization with a KSCN extract of *P. multocida* stimulated development of secretory IgA and serum IgG activity against that extract, and that this response was enhanced by coadministration of cholera toxin, a potent adjuvant for the mucosal immune system. Rabbits immunized in this manner had less severe infections and experienced less severe disease following challenge with live *P. multocida*. The current experiment examined the development of protective immunity following oral immunization with KSCN extracts of *P. multocida* delivered via an alginate microsphere preparation.

Experimental Methods

Male Pasteurella-free rabbits (HRP, Inc., Kalamazoo, Mich.) weighing +5 lb. were used for all studies. Animals were housed in stainless steel cages and allowed ad libitum access to food and water. Before immunization, the nasal cavity of each rabbit was cultured for *P. multocida*.

The Potassium thiocyanate (KSCN) extract of *P. multocida* was prepared using procedures known to those skilled in the art. Briefly, a fresh bacterial culture of *P. multocida* serotype 3,12,15:D was grown for 24 hours on tryptic soy agar containing 5% sheep blood and harvested in 6 ml of equal parts saline and 1.0M KSCN. This suspension was incubated at 37° C. for 6 hours, whole cells were removed by centrifugation at 8,000×g for 10 min, and the solution was dialyzed extensively against 0.01M Tris-hydrochloride—0.32M NaCl—0.01% NaN$_3$ buffer. The extract was concentrated with a Centriprep- and adjusted to a protein concentration of 1 mg/ml with Tris buffer.

KSCN extracts of *P. multocida* were incorporated into alginate microspheres made by the air atomization technique as described in Example 1. Microspheres were prepared to contain 1 mg/ml of KSCN extract protein, 1 mg/ml of KSCN extract protein with 3200 µg/ml of cholera toxin, or no extract protein. Groups of 5 rabbits were immunized by placing 5 ml of suspended microspheres in the drinking water initially (day 0) and 7 and 14 days later. In addition, groups of rabbits were immunized with 5 mg of KSCN extract protein with or without cholera toxin in the drinking water, or 1 mg of KSCN extract protein administered intranasally. One nonimmunized-nonchallenged group was also included. Rabbits were given only a portion of the normal drinking water overnight to assure full consumption of drinking water containing microspheres. Serum and nasal lavage samples were collected prior to initial immunization and at 10, 16 and 21 days later.

Samples were assayed by ELISA for anti-KSCN extract according to procedures known to those of ordinary skill in the art. Briefly, polystyrene microtiter plates were coated with 1 µg of KSCN extract protein per well. Following extensive washing, dilutions of serum (1:25) and nasal lavage (1:2) were added and plates were incubated overnight. Plates were again washed and dilutions of goat anti-rabbit IgA (Accuracte Chemical, Inc., Westbury, N.Y.) or goat anti-rabbit IgG (Sigma Chemical Co., St. Louis, Mo.) were added. Following overnight incubation and extensive washing, substrate (o-phenylenediamine) was added and optical density of wells measured 30 minutes later at 490 nm on a Vmax microtiter plate reader (Molecular Devices, Inc., Menlo Park, Calif.). Specific immunoglobulin activity is expressed as optical density at 490 NM per 30 min.

To examine the development of protective immunity, groups of rabbits were immunized as above and challenged intranasally at day 16 with 1.0×10$^6$ CFUs of *P. multocida*. The nonimmunized group was not challenged. One week after challenge, rabbits were euthanized by IV overdose of sodium pentobarbital. Nasopharyngeal swabs were vortexed vigorously in 1.0 ml of sterile phosphate buffered saline (PBS), and 100 µl of this suspension cultured overnight at 37° C. on TSA with 5% blood. One gram of lung from the apical portion of the cardiac lobe of each rabbit was macerated and vortexed in 1.0 ml of sterile PBS, and 100 µl of this suspension was cultured. CFUs from nasopharyngeal and lung samples were counted after 24 hours of growth. The liver and both tympanic bullae from all rabbits were similarly cultured for the presence of *P. multocida*.

Means and standard errors of ELISA absorbance values and CFUs of cultured *P. multocida* per sample were compared using the Wilcoxon rank sum test. Statistical significance was reached when p.≦0.05. Table 5 shows that rabbits vaccinated orally with antigen-free alginate microspheres and with KSCN extracts in water without using microspheres had minimal antigen specific IgA antibodies in serum or nasal washes. The use of cholera toxin in the oral administration of KSCN extracts helped only modestly. The optical density (O.D.) ELISA value increased about 3 times to 0.145 at day 21 for rabbits orally administered KSCN extracts in microsphres. However, rabbits vaccinated orally with microspheres or intranasally with KSCN extracts had increased anti-*P. multocida* IgA antibodies in nasal washings and IgG in serum. The titers peaked at an O.D. of 0.600 by day 21. These results indicate that cholera toxin did not enhance the immune response to KSCN extracts whether administered within alginate microspheres or not.

TABLE 5

Change in optical density of IgA present in nasal lavage of rabbits inoculated with KSCN extracts of *P. multocida*.

| Group | Day 0 | Day 10 | Day 16 | Day 21 |
|---|---|---|---|---|
| Non-immunized | .025 | .070 | .050 | .050 |
| Microspheres by oral | .065 | .050 | .030 | .050 |
| KSCN by oral | .060 | .090 | .125 | .140 |
| KSCN + cholera toxin by oral | .050 | .105 | .135 | .145 |
| KSCN by Intranasal | .058 | .130 | .500 | .530 |
| KSCN by oral in microspheres | .055 | .140 | .560 | .600 |
| KSCN by oral in microspheres with cholera toxin | .070 | .135 | .610 | .725 |

KSCN: Potassium, thiocyanate extracts of outer membrane proteins.

The ultimate test of a vaccine delivery system is the determination of protection of vaccinated animals following challenge with a pathogen. To test the orally administered vaccine compositions' ability to protect against infection, rabbits were challenged with an intranasal instillation of viable *P. multocida* 7 days after the last dose of vaccine. The rabbits were euthanized 3 days after challenge and serum and nasal washes were assayed for antibodies specific for the KSCN extracts of *P. multocida*. The number of bacteria isolated from nares, lungs, and liver and tympanic bullae is shown in Table 6. The number of bacteria in the lung and nasopharynx in rabbits inoculated orally with antigen-free microspheres or KSCN extracts alone were mere than 70 and 300, respectively.

TABLE 6

Isolation of bacteria from tissues following intranasal challenge in immunized rabbits.

| Group | Positive Cultures | Number of Bacteria in Lung | Number of Bacteria in Nasopharynx |
|---|---|---|---|
| Nonimmunized & Non-challenged | 0/15 | 0 | 0 |
| Microspheres | 7/15 | 84 ± 6 | 321 ± 11 |
| KSCN Oral | 4/15 | 73 ± 2 | 302 ± 9 |
| KSCN + CT Oral | 4/15 | 69 ± 7 | 287 ± 13 |
| KSCN Intranasal | 1/15 | 38 ± 7 | 198 ± 14 |
| KSCN Oral in Microspheres | 3/15 | 40 ± 3 | 205 ± 15 |
| KSCN oral in Microspheres with CT | 1/15 | 40 ± 4 | 188 ± 10 |

Five rabbits per group. Liver and right and left tympanic bullae were cultured from each rabbit. KSCN = potassium thiocyanate extracts of outer membrane proteins; CT = cholera toxin.

The addition of cholera toxin to the KSCN extracts for oral administration did not decrease the numbers appreciably. On the other hand, the number of bacteria isolated from rabbits inoculated orally with KSCN extracts in microspheres, or intranasally, were about 40 and 200 for lung and nasopharynx, respectively. These values are the same as those obtained by intranasal administration of the KSCN extracts. Table 6 clearly demonstrates that the oral administration of KSCN extracts of *P. multocida* in alginate microspheres stimulated protective immunity in other mucosal surfaces than the gut. This is the first example of the stimulation of protective immunity at another mucosal site in animals by oral administration of vaccines using alginate microspheres.

We claim:

1. A vaccine composition for oral administration to vertebrate species to stimulate an immune response in the vertebrate species against a preselected antigen through contact of the antigen with a gut-associated lymphoid tissue of the vertebrate species, said composition comprising an antigen formulation in a delivery vehicle consisting essentially of an alginate gel, said antigen being present in an amount effective to induce an immune response in said vertebrate, wherein the alginate gel enhances the immune response against the preselected antigen.

2. The vaccine composition of claim 1 wherein the alginate gel is in the form of discrete particles.

3. A vaccine composition for oral administration to vertebrate species to stimulate an immune response in the vertebrate species against a preselected antigen through contact of the antigen with a gut-associated lymphoid tissue of the vertebrate species, said composition comprising an antigen formulation in a delivery vehicle consisting essentially of an alginate gel and a polymer coating on the alginate gel, said antigen being present in an amount effective to induce an immune response in said vertebrate, wherein the alginate gel enhances the immune response against the preselected antigen.

4. The vaccine composition of claim 1 wherein the antigen is live virus or bacteria.

5. A vaccine composition for oral administration to ruminant species to stimulate an immune response in said species against a preselected antigen, said composition comprising the preselected antigen in an amount effective to induce an immune response in said species, said antigen dispersed in alginate gel in particulate form, and a hydrophilic carrier matrix for said antigen-containing alginate gel particles, said alginate gel particles being dispersed within the hydrophilic carrier matrix, wherein said carrier matrix is formed to carry at least some of the dispersed particles into the post-ruminal portion of the digestive tract of said ruminant species.

6. The vaccine composition of claim 5 wherein the alginate gel particles are coated with a polymer.

7. The vaccine composition of claim 5 wherein the alginate gel particles have an average diameter of about 1 to about 30 microns.

8. The vaccine composition of claim 7 wherein the alginate gel particles are coated with a polymer.

9. The vaccine composition of claim 5 wherein the antigen is live virus or bacteria.

10. A method of vaccinating a vertebrate species, said method comprising the step of orally administering to said vertebrate species the vaccine composition of claim 1.

11. A method of vaccinating a ruminant species comprising the step of administering orally to said species the vaccine composition of claim 5.

12. A method of stimulating a cell-mediated immune response in avian species comprising the step of orally administering a vaccine composition of claim 1.

13. A vaccine composition consisting essentially of an antigen, in an amount effective to induce an immune response to said antigen, an alginate gel, and a pharmaceutically acceptable carrier, wherein the alginate gel enhances the immune response against the antigen.

14. The vaccine composition of claim 13 wherein the alginate gel is in the form of discrete particles and the antigen is dispersed within the alginate gel particles.

15. A vaccine composition consisting essentially of an alginate gel, an antigen dispersed in the alginate gel, a polymer coating on the alginate gel, and a pharmaceutically acceptable carrier, wherein the alginate gel enhances the immune response against the preselected antigen.

16. The vaccine composition of claim 15 wherein the alginate gel is in the form of discrete particles.

17. The vaccine composition of claim 14 wherein the antigen is live virus or bacteria.

* * * * *